United States Patent
Kim et al.

(10) Patent No.: US 7,416,564 B2
(45) Date of Patent: Aug. 26, 2008

(54) POROUS BIOCERAMICS FOR BONE SCAFFOLD AND METHOD FOR MANUFACTURING THE SAME

(75) Inventors: Hyoun-Ee Kim, Seoul (KR); Hea-Won Kim, Gyungju (KR)

(73) Assignee: Seoul National University Industry Foundation, Seoul (KR)

( * ) Notice: Subject to any disclaimer, the term of this patent is extended or adjusted under 35 U.S.C. 154(b) by 502 days.

(21) Appl. No.: 10/723,401

(22) Filed: Nov. 26, 2003

(65) Prior Publication Data

US 2005/0113934 A1    May 26, 2005

(51) Int. Cl.
A61F 2/28 (2006.01)
A61L 27/32 (2006.01)

(52) U.S. Cl. ................................. 623/23.56; 427/2.27
(58) Field of Classification Search ............. 623/23.56, 623/23.61; 427/2.26, 2.27
See application file for complete search history.

(56) References Cited

U.S. PATENT DOCUMENTS

2003/0099762 A1* 5/2003 Zhang et al. .................. 427/2.1

FOREIGN PATENT DOCUMENTS

KR   2000-2933   1/2000
KR   2000-18897  4/2000

OTHER PUBLICATIONS

Authors Hae-Won Kim, Yoon-Jung Noh, Young,-Hag Koh, Hyoun-Ee Kim and Hyun-Man Kim; Title: Effect of $CaF_2$ on densification and properties of hydroxyapatite-zirconia composites for biomedical applications; Date: Received Dec. 12, 200—Accepted Apr. 18, 2002 Pertinent pp. 4113-4121.
Authors: Hae-Won Kim, Seung-Yong Lee, Chang-Jun Bae, Yoon-Jung Noh, Hyoun-Ee Kim, Hyun-Man Kim, Jea Seung Ko; Title: Porous $ZrO_2$ bone scaffold coated with hydroxyapatite with flouraplatite intermediate layer; Date: Received Nov. 10, 2002—accepted Mar. 9, 2003.

* cited by examiner

Primary Examiner—Bruce Snow
(74) Attorney, Agent, or Firm—Schmeiser, Olsen & Watts LLP (57) ABSTRACT

The present invention provides a porous bioceramics for bone scaffold. The porous bioceramics according to the present invention comprises a biocompatible porous ceramic substrate having the property to thermal-decompose hydroxyapatite in contact with it; a fluorapatite (FA) inner layer formed on said porous ceramic substrate; and a hydroxyapatite (HA) outer layer formed on said fluorapatite inner layer. The insertion of FA intermediate layer can prevent the thermal reaction between $ZrO_2$ and HA. Therefore, the present invention can provide the implant material into human body having excellent mechanical properties of zirconia as well as the biocompatibility, bioaffinity and bioactivity of HA. The present invention can also provide the implant material to promote osteoconduction and osteointegration in human body.

6 Claims, 8 Drawing Sheets

POROUS BIOCERAMICS FOR BONE SCAFFOLD AND METHOD FOR MANUFACTURING THE SAME

FIELD OF THE INVENTION

The present invention relates to a porous bioceramics for bone scaffold, and more particularly, to a porous bioceramics for bone scaffold having excellent biocompatibility, bioaffinity and bioactivity with good mechanical properties together by forming a hydroxyapatite layer on a biocompatible porous ceramic substrate.

BACKGROUNDS OF THE INVENTION

Hydroxyapatite (HA) has very similar crystallographic and chemical properties to hard tissues such as bones and teeth of human body. Therefore, when it is implanted into a human body, it can naturally bind with surrounding tissues without adverse reaction with the tissues of human body. Actually, HA is composed of 95% or more of tooth enamel, and the bone is a composite of fibrous protein, collagen and about 65% of HA. Due to such excellent bioactivity, HA has been given a great deal of attention as a material to replace for the loss of teeth and bones. However, HA has a shortcoming that it is not good in mechanical properties such as mechanical strength and fracture toughness. Thus, it is not proper for use as a material for hard tissues of human body requiring high mechanical strength or fracture toughness such as artificial teeth or hip joints. It is only limited to be used in the part not requiring high mechanical strength such as ear-inside bones.

In order to supplement such lower mechanical properties of HA, material complexation of HA with metal or other ceramics having high mechanical properties has been tried to use the bioaffinity and bioactivity of HA. However, HA may decompose with dehydration due to its contact to the metal or ceramics at the time of heating process in the fabrication of the composite. This reaction produces tricalcium phosphate (TCP), tetracalcium phosphate, calcium oxide and so on, which may form new phases to deteriorate the biological and mechanical properties of HA. Accordingly, there has been a need of new means to prevent the thermal decomposition of HA due to the contact of HA with metal or other ceramics.

As such means, Korean Patent Laid-Open No. 2000-18897 (laid-open date: Apr. 6, 2000) disclosed a method for coating a thin layer of HA on a titanium or its alloy substrate having excellent mechanical properties in an electron beam deposition manner. This method can avoid the decomposition of HA due to thermal treatment by performing the processes at a lower temperature, even particularly, below room temperature.

As another means, Korean Patent Laid-Open No. 2000-2933 (laid-open date: Jan. 15, 2000) disclosed a method for manufacturing a sintered ceramic composite for implant having an inserted alumina barrier layer between zirconia and apatite layers by mixing apatite powder and zirconia powder coated with an alumina precursor and sintering them. This method is to enhance the fracture toughness of the composite by inserting as a barrier layer between zirconia and HA, alumina which has lower tendency of changing HA to β-tricalcium phosphate than that of zirconia during thermal treatment.

SUMMARY OF THE INVENTION

It is an object of the present invention to provide a porous bioceramics for bone scaffold having high mechanical properties without deterioration of biocompatibility and bioactivity of HA.

It is another object of the present invention to provide a porous bioceramics for bone scaffold having proper size of pores and porosity as well as applicable mechanical properties in human body to promote fast tissue reaction and osteointegration due to its large specific surface area.

It is still another object of the present invention to provide a porous bioceramics for bone scaffold in which HA is in dense contact to the porous ceramic substrate with sufficient adhesive strength, therefore there being no delamination or cracks at the interfaces.

It is still another object of the present invention to provide a porous bioceramics for bone scaffold without any problems due to the thermal difference between the HA coating layer and porous ceramic substrate.

It is still another object of the present invention to provide a porous bioceramics for bone scaffold which can control its dissolution rate and biological properties in human body. Such control of its dissolution rate and biological properties can be achieved by adjusting the thickness of HA and fluorapatite (FA) layers, making a composition of HA with other bioactive materials of calcium phosphates, or forming a layer of other bioactive materials of calcium phosphate distinct from the HA layer.

It is still another object of the present invention to provide a method for manufacturing the same. According to the method of the present invention, the porosity of the porous ceramic substrate can be adjusted appropriately.

In order to achieve these and other objects, the present invention provides a porous bioceramics for bone scaffold. The porous bioceramics according to the present invention comprises a biocompatible porous ceramic substrate having the property to thermal-decompose hydroxyapatite in contact with it; a fluorapatite (FA) inner layer formed on said porous ceramic substrate; and a hydroxyapatite (HA) outer layer formed on said fluorapatite inner layer.

Wherein it is preferable that the average size of pores in the porous ceramic substrate is 100 micron or more, and the pores are connected with each other. The porous ceramic substrate is preferably made of zirconia ($ZrO_2$), more preferably, yttria ($Y_2O_3$) stabilized $ZrO_2$. It also has preferably, a porosity in the range between 92% and 74%, and It also has preferably, a compressive strength in the range between 1.6 MPa and 35 MPa. It is preferable that the adhesive strength of HA/FA double layer to the porous ceramic substrate is in the range of 20~30 MPa.

Wherein the HA outer layer may be made of a mixture of HA and other bioactive materials of calcium phosphates. The porous bioceramics of the present invention also further comprises a layer coated with one of other bioactive materials of calcium phosphates or their mixture on said HA outer layer.

The present invention also provides to a method for manufacturing a porous bioceramics for bone scaffold. The method of the present invention comprises the steps of: forming a biocompatible porous ceramic substrate having the property to thermal-decompose hydroxyapatite in contact with it; coating a fluorapatite (FA) inner layer on said porous ceramic substrate; and coating a hydroxyapatite (HA) outer layer on said fluorapatite inner layer.

Wherein the step of forming the porous ceramic substrate may comprise the steps of immersing a porous polymer template into the ceramic slurry and drying it; and thermal-treating the porous polymer template infiltrated with the ceramic slurry to burn out the porous polymer template and to obtain the sintered ceramic body. The step of forming the porous ceramic substrate may further comprise repeating the step of immersing and drying (replication process) to adjust the porosity of the porous ceramic substrate.

The step of coating FA inner layer may comprise the steps of immersing the formed porous ceramic substrate into the FA slurry and drying it; and thermal-treating the formed FA inner layer.

The step of coating HA outer layer may comprise the steps of immersing the formed porous ceramic substrate coated with FA inner layer into HA slurry and drying it; and thermal-treating the formed HA outer layer.

DETAILED DESCRIPTION OF THE INVENTION

A more complete appreciation of the invention and many of the attendant advantages thereof can be better appreciated by reference to the following detailed description and the accompanying drawings.

Figure 1:
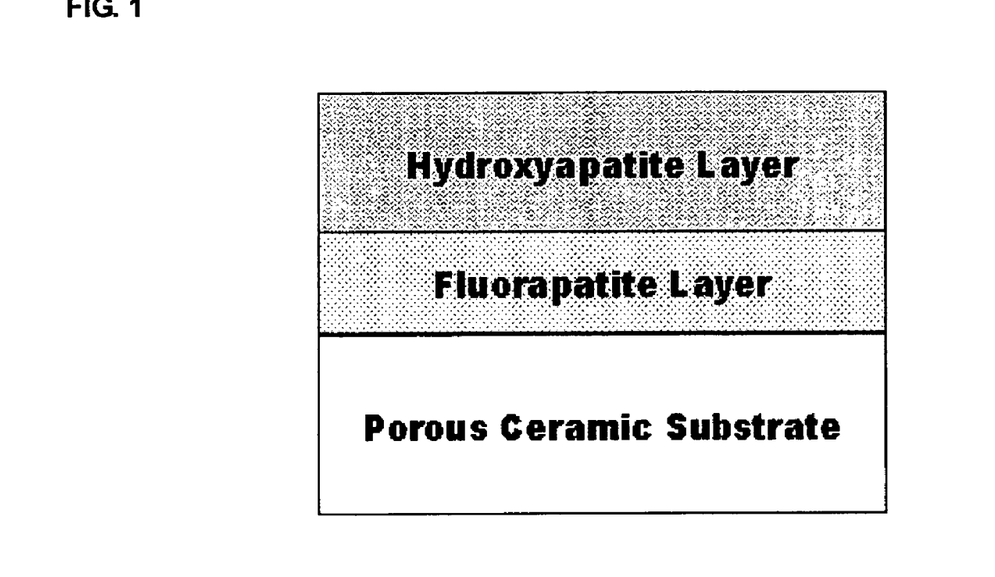
FIG. 1 is a schematic diagram showing the structure of the porous bioceramics according to the present invention.

As shown in FIG. 1, the porous bioceramics of the present invention is formed by coating, in turn, FA inner and HA outer layers on a porous ceramic substrate. Though FIG. 1 shows that the HA/FA layers are coated on one surface of the porous ceramic substrate, but it is actually preferable that they should be coated on the entire surface of the substrate. The porous ceramic body of the present invention has such porous structure with large specific surface area that it can promote fast tissue reaction and osteointegration in human body.

Figure 2A:
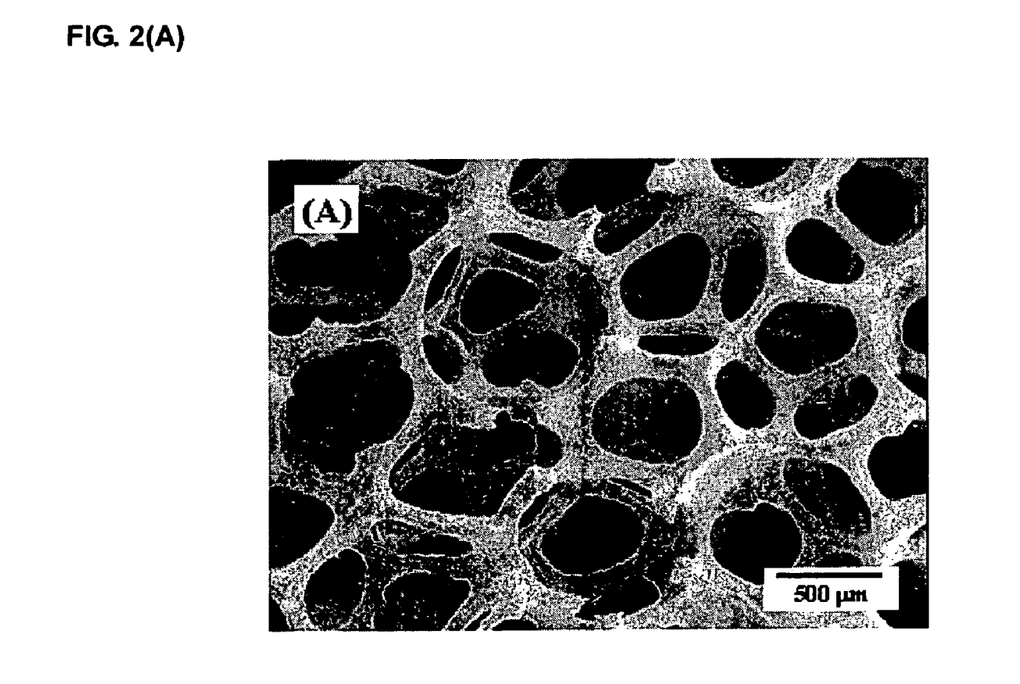
FIGS. 2(A) to (C) are scanning electron microscopy (SEM) micrographs of the porous $ZrO_2$ substrates with a porosity of (A) 92%, (B) 83%, and (C) 74% fabricated according to the examples of the present invention.
Figure 2B:
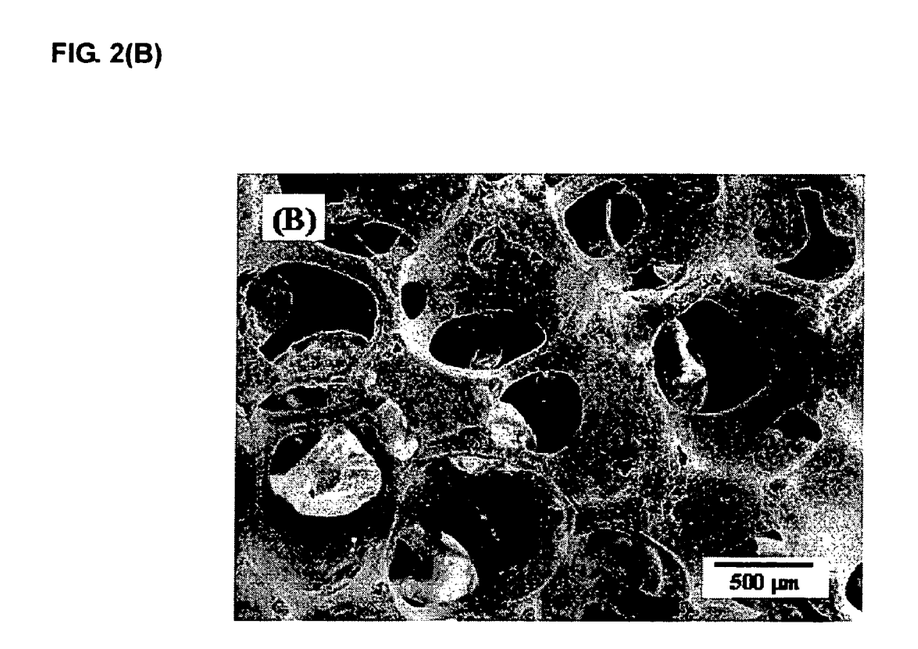
Figure 2C:
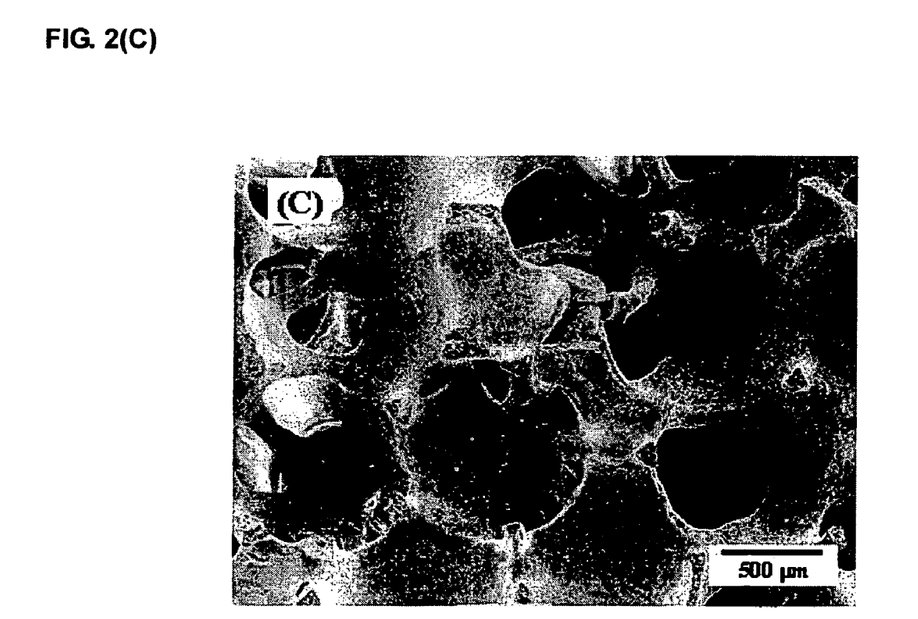

The material of substrate used in the present invention should have good mechanical strength and fracture toughness as well as biocompatibility not to make any problem in human body. Such material may include zirconia ($ZrO_2$), alumina ($Al_2O_3$) and titania ($TiO_2$). Such material is preferably zirconia, more preferably yttria ($Y_2O_3$) stabilized zirconia. As shown in FIG. 2, the substrate used in the present invention should have a framework structure for bone ingrowth into the channels, in which the pores should be interconnected with each other and the pore size be minimum about 50 micron, preferably minimum abut 100 micron. If the size of pores is very small or the pores are severely blocked, fast osteoconduction cannot be induced. The porous ceramic substrate used in the present invention may have preferably, a porosity of 95~65%, more preferably, a porosity of 92~74%, and preferably, a compressive strength of 0.5~100 MPa, more preferably, a compressive strength of 1.6~35 MPa, according to the application parts of human body.

In order to provide a porous bioceramics for bone scaffold having sufficient mechanical properties as well as excellent biocompatibility, bioaffinity and bioactivity of HA, the present invention is to coat HA on a porous ceramic substrate having excellent mechanical properties. However, for example, when HA is directly coated on a zirconia substrate, the direct contact of HA with $ZrO_2$ causes serious decomposition reaction at elevated temperatures, for example at 1150° C. Indeed, the HA coated on the $ZrO_2$ degrades into β- or α-TCP and $CaZrO_3$ according to Eq. (1)

$$Ca_{10}(PO_4)_6(OH)_2 + t\text{-}ZrO_2 = 3Ca_3(PO_4) + c\text{-}ZrO_2/ CaZrO_3 + H_2O \quad (1)$$

The formation of TCP at the interface of HA and $ZrO_2$ may cause serious problems because it is dissolved much faster than HA in a body fluid. This result in a disintegration of the coating layer from the $ZrO_2$ substrate.

In order to prevent such thermal decomposition of HA, the present invention uses FA (fluorapatite) as an intermediate layer between the porous ceramic substrate and the HA layer. The FA has a superior chemical and thermal stability to HA. Hence, the inventors have reviewed the possibility to prevent the thermal reaction between the HA and $ZrO_2$ substrate, with attention to these thermal and chemical properties of FA. As shown in FIG. 5(B), the porous ceramic body of the present invention with HA/FA layers on the $ZrO_2$ substrate does not cause any chemical reactions between FA and $ZrO_2$ at the high temperature of 1250° C. as well as the reaction between HA and $ZrO_2$. This result confirms that the FA layer is usefully available as an intermediate to prevent the thermal reaction between HA and $ZrO_2$ substrate.

FA may be prepared by the following Eq. (2).

$$3Ca_3(PO_4)_2 + CaF_2 = Ca_{10}(PO_4)_6F_2 \quad (2)$$

FA has biological advantages in itself. FA is expected to have the effect of fluoride ion in itself in human body. It is known to have the prevention of caries decay by suppressing dissolution of bones and to play an important role in the formation of bones due to its crystallization enhancement and other properties.

In fabrication of the porous ceramic body of the present invention, the porous ceramic substrate may be prepared with several methods, for example, polymer foam template using method, sol-gel method, extrusion method, and coral using method. The polymer foam template method is for example, to immerse polyurethane sponge into ceramic slurry and dry it, and then to burn out the sponge. This method is easy in control of the porosity and pore size. The key points are in the preparation of ceramic slurry and thermal treatment. The sol-gel method is to prepare ceramic sol and then to obtain the pores in the gelatinazation process. This method can be carried out at a low temperature, but to obtain the products with irregular shapes of pores. Extrusion method is easy in control of the pores distribution in two dimensions and the porosity, but complicate in the fabrication processes. The coral using method is to burn out the coral for removing organic materials and to use the pores of the remnant inorganic materials. Among these methods, the polymer foam template method is most appropriate in the present invention when considering the ease to control the porosity and the pore size and the simplicity of fabrication.

The fabrication method of the porous ceramic substrate using the polymer foam template includes the step of immersing a porous polymer foam template into ceramic slurry and drying it. Wherein, the ceramic slurry may be prepared by mixing a ceramic powder, a dispersant and a binder in water or organic solvent such as alcohol or their mixture. The dispersant is one usually used in conventional slurry preparations, and may include triethyl phosphate (TEP). The binder is one usually used for binding the ceramic powder, and may include polyvinylbutyl (PVB).

Figure 3:
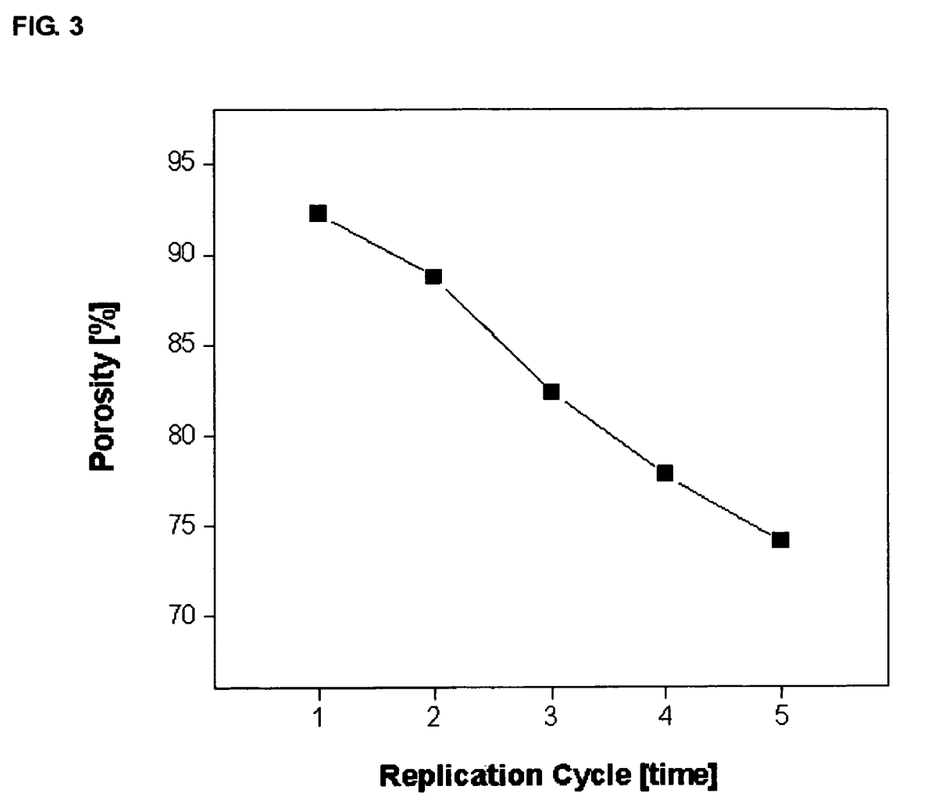
FIG. 3 is a graph showing the porosities of the porous $ZrO_2$ substrates fabricated according to the examples of the present invention with respect to the number of replication process.

Such immersing-drying step may be repeated with several times (replication process). The porosity and compressive strength of the fabricated porous ceramic substrate can be adjusted according to the number of replication cycles. As shown in FIG. 3, the porosity of the yttria stabilized zirconia substrate decreases 74% (5 cycles) from 92% (1 cycle) according to the number of replication cycles. The zirconia substrate also has a compressive strength in the range of 1.6~35 MPa at a porosity in the same range. On the other hand, HA has that in the range of 0.3~5 MPa at same porosity range. In consideration that the purpose of the present invention is to achieve fast osteoconduction and osteointegration with the porous ceramic body having appropriate pore size and that the mechanical strength may be properly selected according to the application parts in human body, the porosity may be adjusted in the range of 95-65% and the compressive strength may also be done in the range of 0.5-100 MPa. It would be considered that these ranges could achieve the purpose of the present invention and the values could be selected according to the application parts.

After the immersing-drying process, the polymer foam template infiltrated with the ceramic slurry is thermal treated to burn out the polymer template and obtain the sintered ceramic substrate. The thermal treatment removes not only the polymer template but also binder and/or dispersant used for the preparation of slurry by burning out them. The thermal treatment may be usually performed at a high temperature of 600° C. or higher. For example, it may be preferably carried out by the two steps of burning out the polymer template and binder at a temperature of about 800° C. and sintering the ceramic body at a temperature of about 1400° C.

It is preferable in the present invention that the FA and HA layers should be formed with the method of coating the slurries prepared from their powders on the porous ceramic substrate. There are several methods to form the ceramic coatings, but the slurry coating method used in the present invention has the following advantages: that the method is economically good because the coating is easy and the equipment is simple; it can be easily applicable to the complicated shapes of substrates; it can easily prepare the relatively thick coatings; it can easily control the thickness of coatings; it can variously adjust the materials of coatings. In addition to the general advantages, the slurry coating method also has the following particular advantages in the present invention: that it allows the framework structure of the porous ceramic substrate to be copied on the coatings although not as it is, therefore providing the structure for more promoting the fast osteoconduction and osteointegration in human body; it can control the dissolution rate and biological properties of the porous ceramic body by adjusting the thickness ratio of HA/FA layers; and also by forming the HA layer with a mixture of HA and other bioactive materials of calcium phosphate.

The formation of FA inner coating may be carried out through the steps of immersing the FA slurry into the porous ceramic substrate, drying and thermal treating it. The FA slurry may be prepared with the same method as described above. The replication of the processes may allow the FA inner layer to have uniform thickness and can control the thickness of FA layer.

The formation of HA outer coating may be carried out in the same manner. It is known that the apatite, particularly, HA may be thermally decomposed when the thermal treatments of apatites are performed at a temperature of near 1300° C. or higher. Therefore, the treatment should be carried out at the lower temperature. Preferably, the treatment may be achieved for example, through the two steps of burning out the binder at 800° C. and sintering the FA and HA at 1200° C. or 1250° C.

As described above, the HA layer may be formed with a mixture of HA and other bioactive materials of calcium phosphates. On the HA layer may also be formed a coating layer of one of other bioactive materials of calcium phosphates or their mixture. Such addition or new layer formation of other bioactive material may provide an advantage of controlling the dissolution rate and biological properties of the porous ceramic body in human body.

EXAMPLES

Fabrication of Porous Ceramic Substrate

As a starting material for the porous ceramic substrate, commercially available $ZrO_2$ powder (3 mol % $Y_2O_3$, Cerac Inc., WI, USA) was used to prepare a slurry mixture. The powder of 100 g was stirred vigorously in 150 ml distilled water dispersed with a triethyl phosphate (TEP; $(C_2H_5)_3PO_4$, Aldrich, USA) of 6 g for 24 h. As a binder, polyvinylbutyl (PVB, Aldrich, USA) of 6 g was dissolved in another beaker, which was subsequently added to the slurry and stirred for an additional 24 h.

A polyurethane foam template (45 ppi, Customs Foam Systems Ltd, Canada) was cut to the appropriate dimensions for fabricating porous scaffolds. The prepared sponge was immersed in the slurry and subsequently blown with an air gun to disperse the slurry uniformly throughout the porous scaffolds without blocking the pores. The sponge was then dried at 80° C. for 10 min. These dipping-and-drying steps were repeated 4 times. The sponge was then oven dried at 80° C. for 12 h. The obtained body was heat treated to burn out the sponge and binder at 800° C. for 5 h at a heating rate of 2° C./min, and at 1400° C. to solidify and finally to obtain a dense $ZrO_2$ porous scaffold.

By repeating the above replication process (2-5 times), it was possible to reduce the porosity of the structure. For the purpose of comparison, a HA porous body was fabricated also from the HA slurry mixture using the same procedure as for $ZrO_2$ with the only difference being the heating cycle; the final heat treatment was done at 1250° C. for 3 h instead.

HA/FA Coating on the Porous Ceramic Substrate

Commercially available HA (Alfa Aesar Co., USA) and in-house fabricated FA powder were used as starting slurries for the coating process. Each powders of 15 g were mixed with TEP and PVB in 50 ml ethanol, and stirred for 24 h to prepare the HA and the FA slurry. The fabricated $ZrO_2$ porous body was immersed in the FA slurry and dried at 80° C. for 3 h. This was followed by heat treatment at 800° C. for 5 h for binder burnout and at 1200° C. for an additional 1 h to prepare the FA coating. The process was repeated twice to obtain a uniform FA layer. The FA-coated body was immersed in the HA slurry, dried and heat-treated following the same procedures. By this repeated process, a HA/FA double-layer coated $ZrO_2$ porous body was obtained. For a comparison, HA was coated directly onto the $ZrO_2$ body without the FA layer.

Characterization and Test

The porosity of the bodies was calculated by measuring their dimensions and weights. Namely, the volumes and weights of the bodies were exactly measured to calculate the densities of the bodies, which were then divided with the theoretical density of the material to obtain relative densities, and the percentages of which were then subtracted from 100 to obtain the porosities of the bodies. For a compressive strength test, porous specimens with dimensions of 5×5×10 mm were axially loaded at a crosshead speed of 0.05 mm/min using universal testing machine. Both edges were impregnated with paraffin to eliminate the edge fracture. The phase and the morphology of the coated bodies were analyzed using X-ray diffraction (XRD) and scanning electron microscopy (SEM), respectively. The adhesion strength of the coating layer was tested with an adhesion testing apparatus (Sebastian V, Quad Group, Spokane, Wash., USA). A stud pre-coated by the manufacturer using an epoxy of a proprietary composition was adhered to the coating layer by curing the epoxy at 150° C. for 1 h. The stud with diameter of 1.69 mm was pulled with a loading rate of about 2 mm/min until the coating layer failed, and the bond strength was calculated from the maximum load recorded.

In Vitro Cellular Assay

The human osteosarcoma (HOS) cell line was used after being cultured in flasks containing Dulbecco's modified Eagle's medium (DMEM, Life Technologies Inc., MD, USA) supplemented with 10% fetal bovine serum (FBS, Life Technologies Inc., MD, USA). The cells were then plated at a density of $1 \times 10^4$ cells/ml on a 24-well plate containing the fabricated porous specimens (HA/FA coated $ZrO_2$, HA, and $ZrO_2$) and cultured for 5 and 21 days in an incubator humidified with 5% $CO_2$/95% air at 37° C. After culturing for 5 days, the morphology of the proliferated cells was observed with SEM after fixation with glutaraldehyde (2.5%), dehydration with graded ethanol (70%, 90%, and 100%), and critical point drying.

For an assessment of the alkaline phosphatase (ALP) activity, the cells were cultured for 21 days. After decanting the culture media, the cell layers were washed once with Hank's balanced salt solution (HBSS), followed by a detachment with Trypsin-EDTA solution for 10 min. After centrifugation at 1200 rpm for 7 min, the cell pellets were washed once with PBS and resuspended by vortexing in 200 ml of 0.1% Triton X-100. The pellets were disrupted further by 7 freezing/thawing cycles. After centrifugation at 13,000 rpm in a microcentrifuge for 15 min at 4° C., the cell lysates were assayed colorimetrically for their ALP activity using p-nitrophenyl phosphate as a substrate at a pH 10.3 (Sigma Kit, as described fully in procedure no. 104). Each reaction was initiated with p-nitrophenyl phosphate, and allowed to react for 60 min at 37° C., which was then quenched on ice. The p-nitrophenol produced was measured at 410 nm using spectrophotometer.

RESULTS AND DISCUSSION $ZrO_2$ Porous Scaffold

Figure 4:
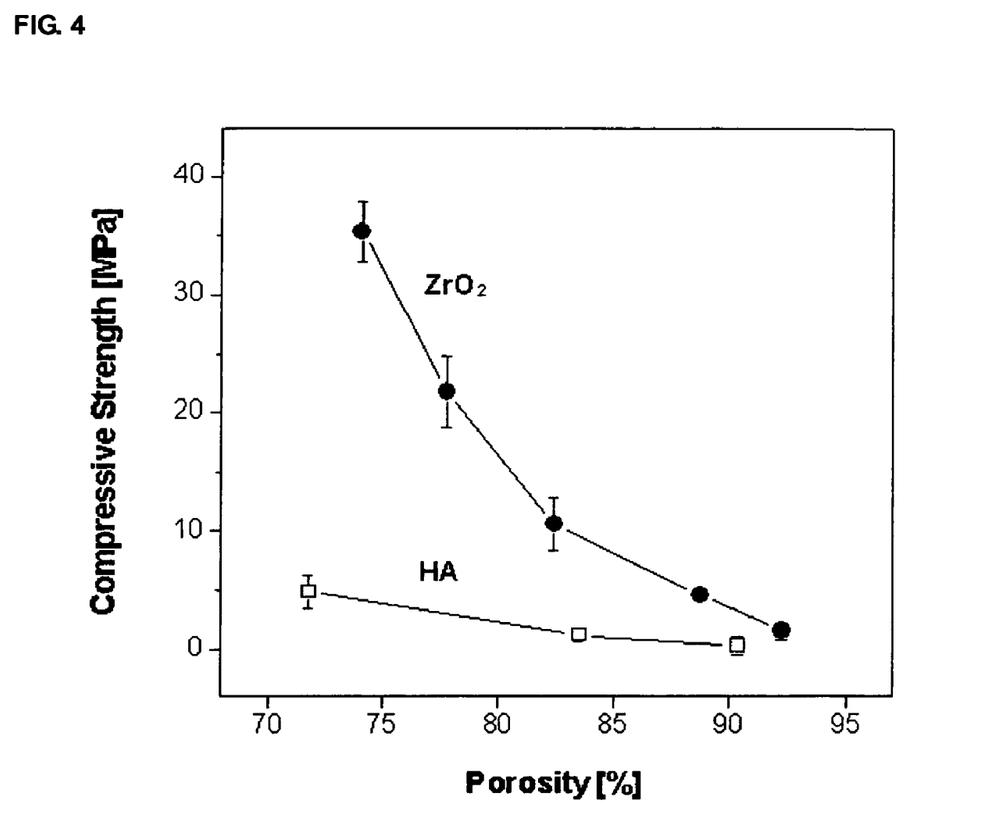
FIG. 4 is a graph showing the compressive strengths of the porous $ZrO_2$ substrates fabricated according to the examples of the present invention as a function of the porosity. These values are compared with those of the porous bodies fabricated with pure HA.

Among many fabrication methods, the reticulated foam approach was adopted in these examples, where the polyurethane template was replicated with ceramic slurries. This was found to be quite effective in obtaining highly porous structures. Typical structures of the as-fabricated $ZrO_2$ porous scaffolds with various porosities are shown in FIGS. 2(A)-(C). By repeating the replication process, it was possible to obtain porous bodies with different degrees of porosity (92-74%). After a single replication, a highly uniform porous structure with the porosity of 92% was obtained (FIG. 2(A)). Spherical macropores with a diameter of about 600 mm and the stems with diameters of 100-200 mm formed a perfectly interconnected pore structure. The shape of the pores and stems maintained the initial polyurethane structure without blocking the pores or destroying the framework. By repeating the replication process three times, the stems became thicker and the porosity decreased to 83%. Even though the initial shape of the framework was slightly altered, there was little blocking of pores (FIG. 2(B)). Further replications decreased the porosity steadily until the pores were partly blocked as shown in FIG. 2(C). However, the body still retained a highly interconnected pore structure with a dense $ZrO_2$ framework. FIG. 3 shows the porosity change of the $ZrO_2$ scaffolds as a function of the replication cycle. The porosity decreased steadily with increasing the replication cycle. An approximately 4-5% reduction in porosity was observed with each cycle. After repeating the procedure for 5 times, a porosity of 74% was obtained. Based on these results, the porosity can be controlled by changing only the number of replication cycles. To investigate the mechanical properties of the fabricated $ZrO_2$ scaffold, the compressive strength was measured and compared with that of pure HA body, as shown in FIG. 4. The strength of $ZrO_2$ was markedly higher than that of pure HA: with equivalent porosities, the strength of $ZrO_2$ was about 7 times higher than that of pure HA. The strength of the $ZrO_2$ ranged from 1.6 to 35 MPa when the porosity was between 92% and 74%, while that of HA was in the range of 0.3-5 MPa with equivalent porosities.

Such porous structures of $ZrO_2$ obtained in these examples are expected to be sufficient to permit tissue ingrowth and anchor the prosthesis to the surrounding bone as well as to supply blood and nutrients to the bone-like vascular canals. When the porosity approached to 70%, the pores were partly blocked as a result of thicker stems, but they were still interconnected with each other. It is therefore expected that the porous body with 70% or slightly less of porosity may be used for the purpose of the present invention.

When considering the compressive strength of cancellous bone (2-12 MPa), the $ZrO_2$ porous structures with several porosities obtained in these examples can possibly be used as load-bearing parts.

Phase and Morphology of HA/FA Coating Layer

Figure 5:
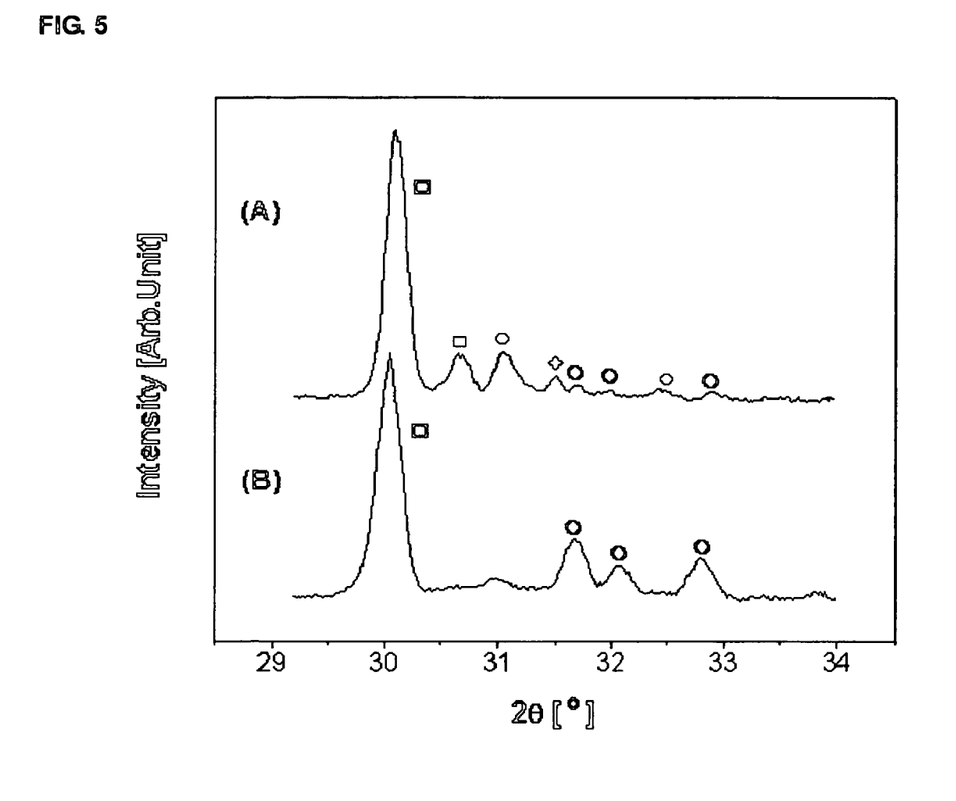
FIGS. 5(A) to (B) are graphs showing the X-ray diffraction (XRD) patterns of the porous $ZrO_2$ bodies coated with HA layer; (A) without the intermediate layer of FA and (B) with the intermediate layer, fabricated according to the examples of the present invention. These figures show the function of the FA inner layer. In the graphs, the symbols in parentheses indicate the peaks by the materials described next to those. (○) HA, (□) $ZrO_2$, (●) β-TCP, (■) α-TCP, and (♦) $CazrO_3$.

The $ZrO_2$ body with the porosity of 92% was coated with HA layer. To prevent chemical reactions between the HA and $ZrO_2$, the FA layer was coated on the $ZrO_2$ surface prior to the HA coating. The effect of the FA intermediate layer on the stability of HA as well as $ZrO_2$ is well illustrated by the XRD patterns shown in FIG. 5.

Without the FA layer, considerable amount of α- and β-TCP as well as $CaZrO_3$ was formed after heat treatment at 1250° C., as shown in FIG. 5(A). Naturally, the HA peaks were very weak, confirming the reaction between HA and $ZrO_2$. On the other hand, when the FA was pre-coated, no such reaction products were detected as shown in FIG. 5(B). These results clearly illustrate the effect of the FA layer on suppressing the reactions between HA and $ZrO_2$.

Figure 6A:
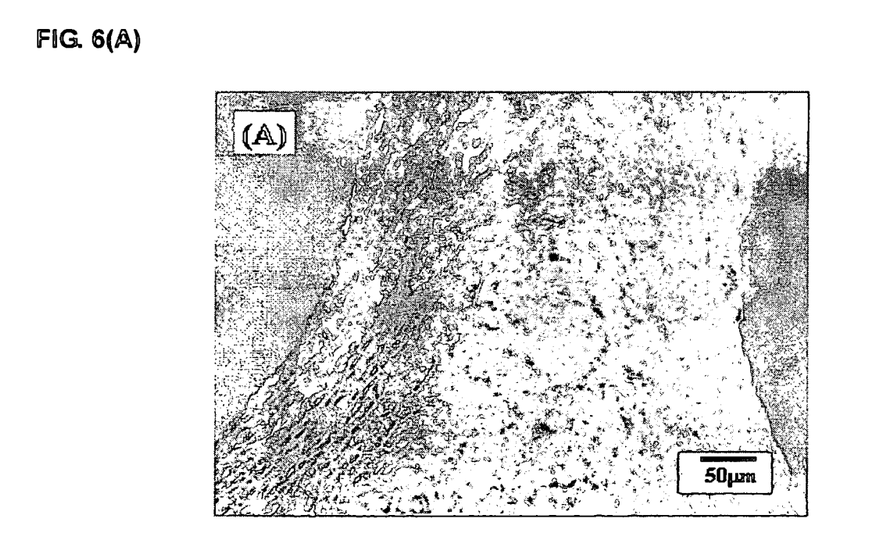
FIGS. 6(A) to (B) are SEM micrographs of porous $ZrO_2$ body coated with HA/FA layers fabricated according to an example of the present invention, (A) at low and (B) at high magnification.
Figure 6B:
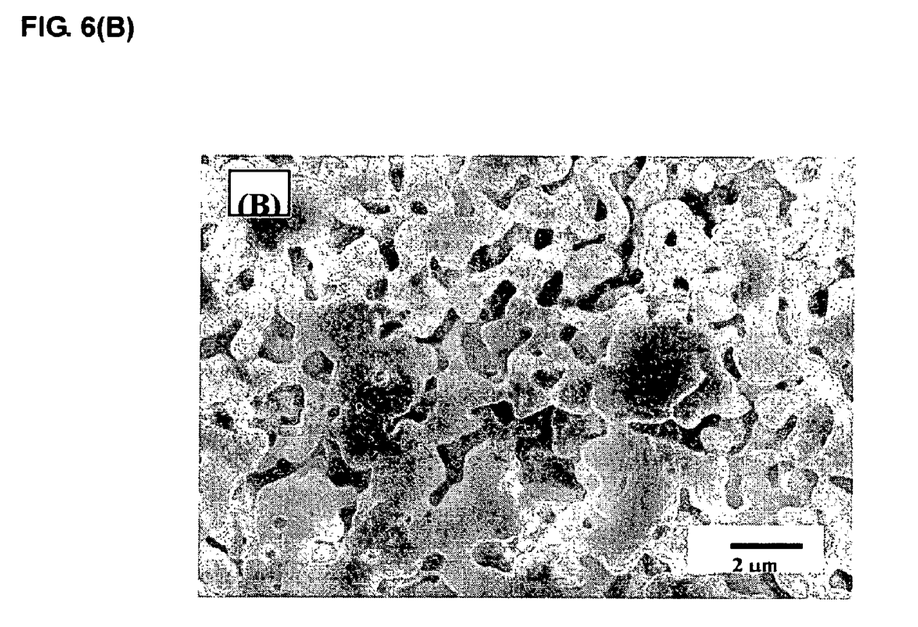
Figure 6C:
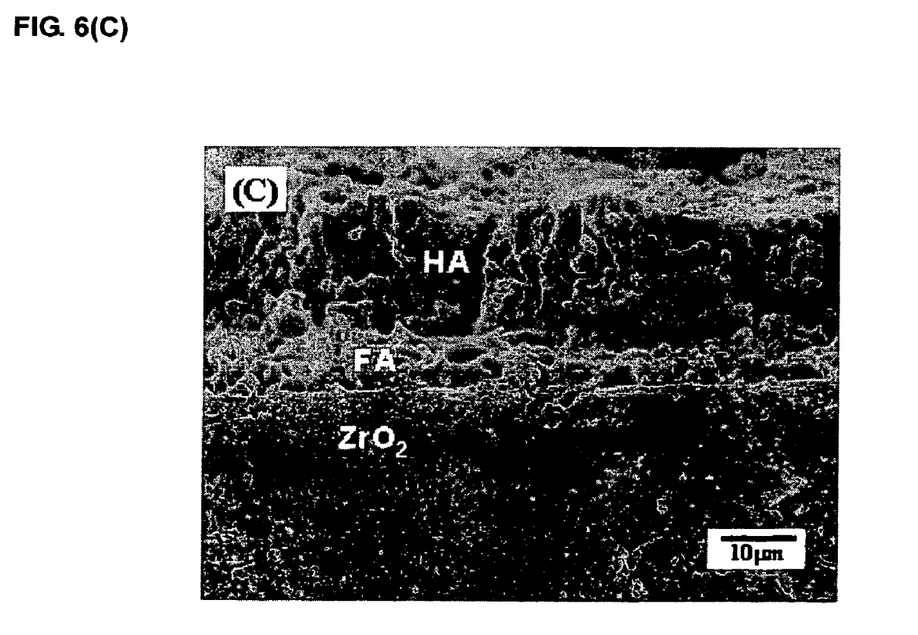
Figure 7:
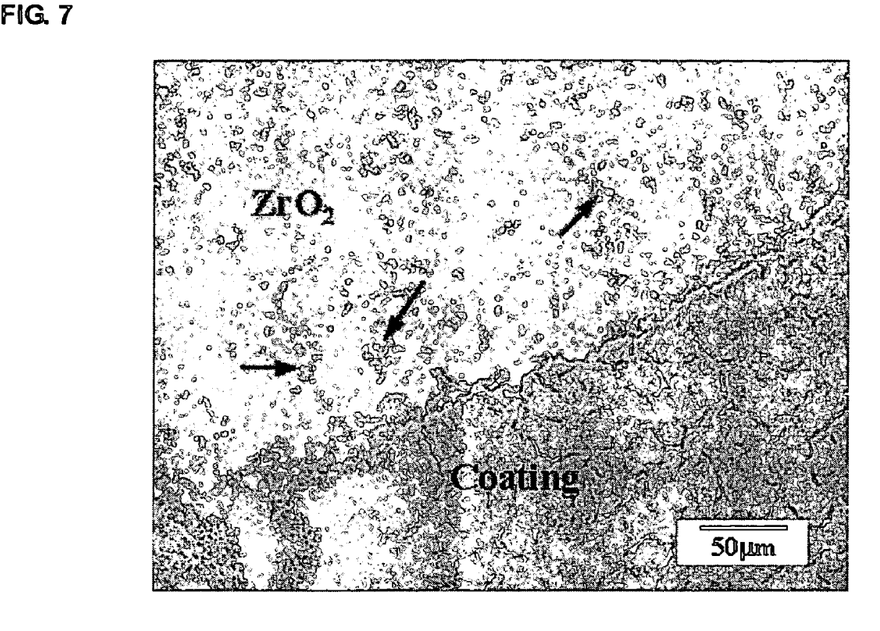
FIG. 7 is a SEM micrograph on detached area of the coating layer after the delamination of the coating layer from the HA/FA coated porous $ZrO_2$ body fabricated according to an example of the present invention.

The SEM morphologies of HA/FA coating layer on $ZrO_2$ are shown in FIG. 6. The $ZrO_2$ framework was uniformly coated with HA/FA as shown in FIG. 6(A). A cross section also shows a uniform coating layer with thickness of about 30 mm (FIG. 6(B)). At higher magnification, the HA layer was distinguishable from the FA layer as shown in FIG. 6(C). The thicknesses of the FA and HA layers are about 5 and about 20 mm, respectively. There were no delamination or cracks at both interfaces of HA/FA and FA/$ZrO_2$, indicating relatively tight bondings among the layers. The bond strength was in the range of 20-30 MPa without much variation depending on the heat treatment temperature. The detached surface was observed with SEM after the strength test. The failure occurred mainly at the FA/$ZrO_2$ interface as shown in FIG. 7. However, fragments of the coating layer still remained on the surface (arrows), which was confirmed by EDS analyses.

These results show that the adhesive strength between FA and $ZrO_2$ is lower than that between HA and FA. The bonding between the HA and the FA in the HA/FA double layer appeared to be very high as observed by the SEM micrographs. This was attributed to the similarity in the chemical composition, crystallographic structure, and the sintering behaviors between the HA and the FA.

The structure of the coating layer was rather porous with pore sizes of 1-2 mm. The microporous structure of the coating layer can induce an improved adhesion of the bone with implants through mechanical interlocking and consequently promote osteointegration. Moreover, the microporous structure has an advantage for the circulation of a physiological fluid through the coating and can therefore enhance the ingrowth of bone into the coating layer. The intrinsic mechanical properties of the coating layer, such as the toughness and hardness, are expected to be somewhat down regulated due to the micro-porous structure. In a coating system, bonding strength of the coating layer to the substrate is one of the most crucial parameters that determines the stability and longevity of the system. A poor bonding may result in a loss of fixation from the host tissues at the interface. The value obtained in the HA/FA coated $ZrO_2$ was about 22 MPa, which was comparable to or slightly higher than the reported values of HA coated metal substrate by sol-gel method(Liu DM, Yang Q, Troczynski T. Sol-gel hydroxyapatite coatings on stainless steel substrates. Biomaterials 2002;23: 691-8; Weng W, Baptista J L. Preparation and characterization of hydroxyapatite coating on $Ti_6Al_4V$ alloy by a sol-gel method. J Amer Ceram Soc 1999;82:27-32.). The relatively high bonding strength was attributed to the relief of thermal mismatch between the HA/FA and $ZrO_2$ (due to porous structure of the coating layer) and also to the chemical inertness of FA with respect to $ZrO_2$ substrate.

Cellular Responses

Figure 8A:
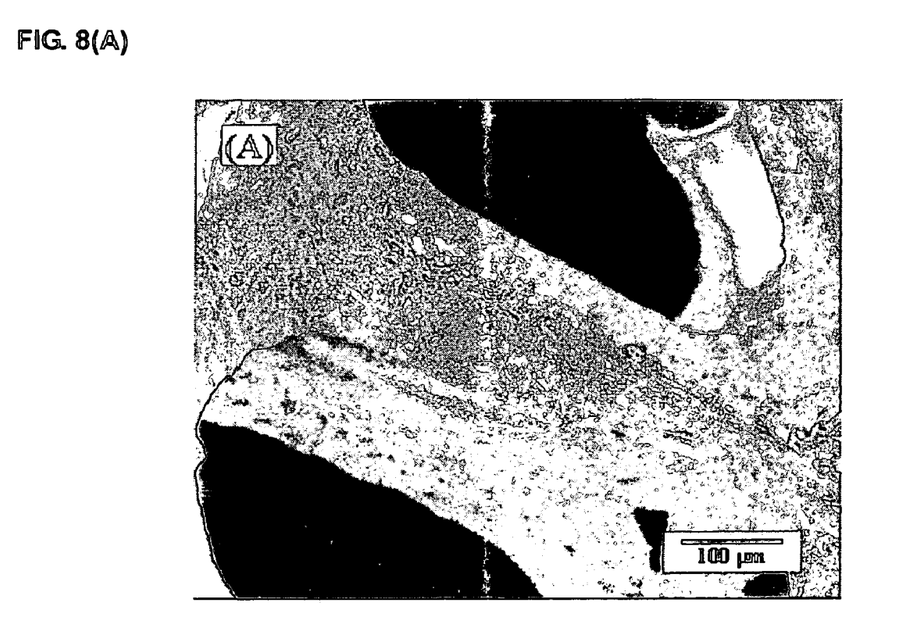
FIGS. 8(A) to (B) are SEM micrographs showing the proliferated HOS cells on the HA/FA coated porous $ZrO_2$ body fabricated according to an example of the present invention after culturing for 5 days, (A) at low and (B) at high magnification.
Figure 8B:
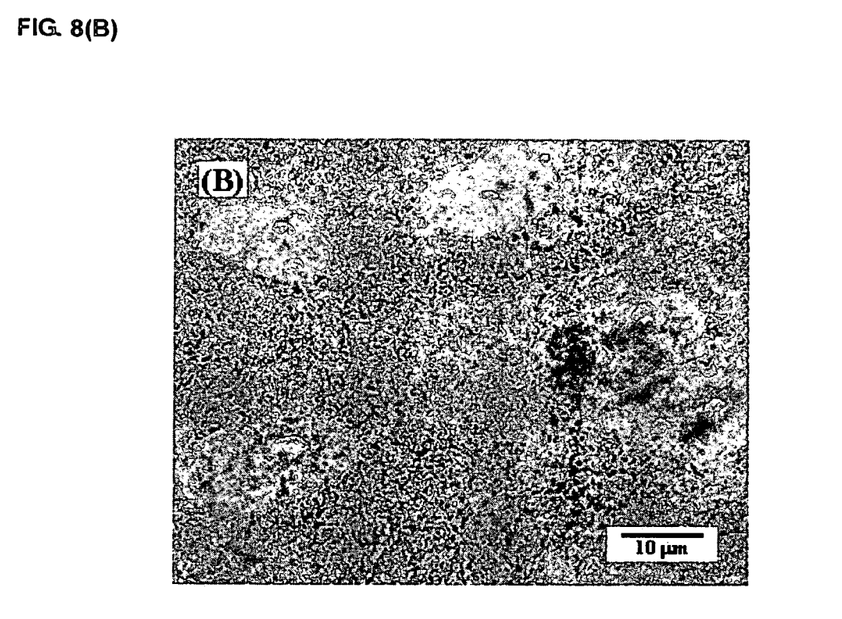
Figure 9:
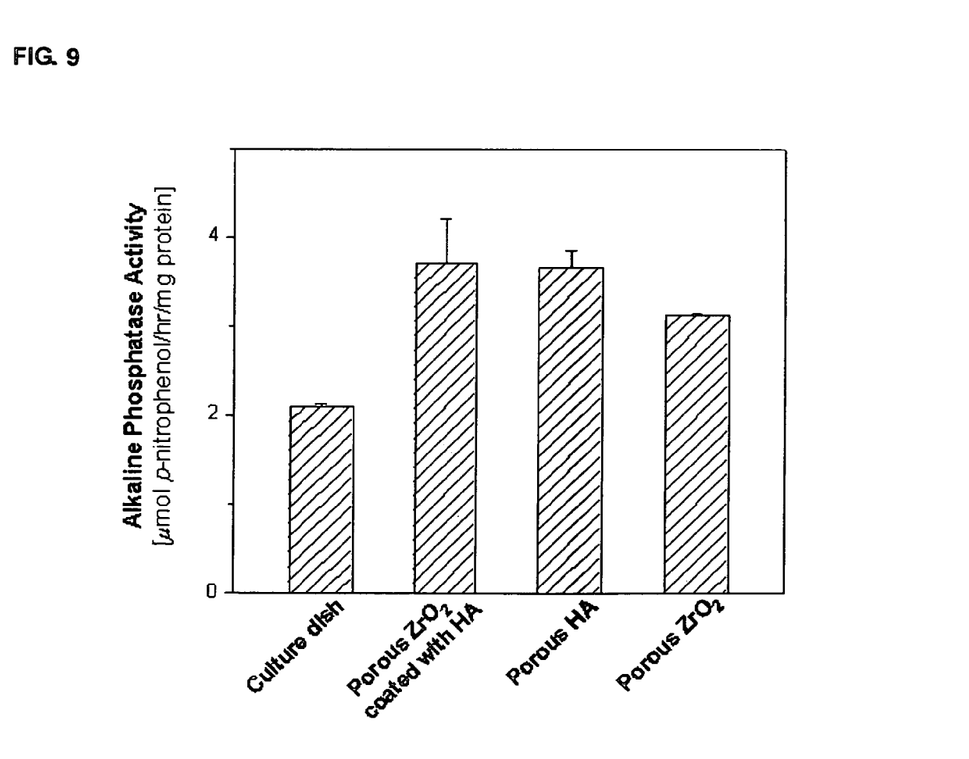
FIG. 9 is a graph showing the alkaline phosphatase (ALP) activity of HOS cells on HA/FA coated $ZrO_2$ porous scaffold fabricated according to the example of the present invention after culturing for 21 days. In the graph are indicated the values for plastic cell culture dish used as a control, HA coated $ZrO_2$ porous body, pure HA porous body and pure $ZrO_2$ porous body.

For an assessment of the cellular response to the HA/FA coated $ZrO_2$ scaffolds, the osteoblast-like HOS cells were seeded on the fabricated materials. FIG. 7 show the cell growth morphologies on the HA/FA coated $ZrO_2$ after culturing for 5 days. The cells spread well and migrated deep into the large pores, suggesting the osteoconducting characteristics of the porous scaffolds (FIG. 7(A)). The cells were uniformly proliferated throughout the porous structure. At higher magnification, it is clearly observed that the cell membranes spread well with an intimate contact with the coated surface, as shown in FIG. 7(B). The differentiation characteristics of the cells were evaluated by the ALP expression level after culturing for 21 days, as shown in FIG. 8. Pure HA with the same structure and $ZrO_2$ without coating were also tested for the purpose of comparison. The ALP activities of the HOS cells on all porous materials showed higher ALP expression level compared to the cell culture dish. In particular, the HA/FA coated $ZrO_2$ sample exhibited a similar ALP expression level with respect to the pure HA body. As expected, the differentiation on the $ZrO_2$ without coating was lower than that on the coated sample.

While the present invention has been shown and described with reference to certain preferred embodiments thereof, it will be understood by those skilled in the art that various changes in form and details may be made therein without departing from the spirit and scope of the invention as defined by the appended claims.

What is claimed is:

1. A method for manufacturing a porous bioceramics for bone scaffold comprising the steps of:
    forming a biocompatible porous ceramic substrate having the property to thermal-decompose hydroxyapatite in contact with it, wherein the average size of pores in said porous ceramic substrate is 100 micron or more, and the pores are connected with each other;
    coating a fluorapatite (FA) inner layer on said porous ceramic substrate; and
    coating a hydroxyapatite (HA) outer layer on said fluorapatite inner layer, wherein the step of coating the HA outer layer comprises the steps of immersing the formed porous ceramic substrate coated with the FA inner layer into HA slurry and drying it; and thermal-treating the formed HA outer layer, and wherein the step of thermal-treating comprises sintering at a temperature in the range of from about 1200° C. to about 1250° C.

2. The method according to claim 1, wherein the step of forming said porous ceramic substrate comprises the steps of immersing a porous polymer template into the ceramic slurry and drying it; and thermal-treating the porous polymer template infiltrated with the ceramic slurry to burn out the porous polymer template and to obtain the sintered ceramic body.

3. The method according to claim 2, wherein the step of forming said porous ceramic substrate further comprises repeating the step of immersing and drying to adjust the porosity of said porous ceramic substrate.

4. The method according to claim 1, wherein the step of coating FA inner layer comprises the steps of immersing the formed porous ceramic substrate into the FA slurry and drying it; and thermal-treating the formed FA inner layer.

5. The method according to claim 1, wherein said HA outer layer is made of a mixture of HA and other bioactive materials of calcium phosphates.

6. The method according to claim 1, wherein it further comprises the step of coating one of other bioactive materials of calcium phosphates or their mixture on said HA outer layer.

* * * * *